United States Patent [19]

Hirohara et al.

[11] 4,108,723
[45] Aug. 22, 1978

[54] METHOD FOR OPTICAL RESOLUTION OF DL-LYSINE COMPOUNDS

[75] Inventors: Hideo Hirohara; Shigeyasu Nabeshima, both of Ibaraki; Tsuneyuki Nagase, Takatsuki, all of Japan

[73] Assignee: Sumitomo Chemical Company, Limited, Osaka, Japan

[21] Appl. No.: 829,945

[22] Filed: Sep. 1, 1977

[30] Foreign Application Priority Data

Sep. 8, 1976 [JP] Japan .................................. 51-108277

[51] Int. Cl.$^2$ .............................................. C07B 19/02
[52] U.S. Cl. ........................................ 195/2; 195/3 R; 195/29; 195/30; 195/DIG. 11
[58] Field of Search ............................. 195/2, 3 R, 29

[56] References Cited

U.S. PATENT DOCUMENTS 3,816,254  6/1974  Chibata et al. ............................ 195/2
3,963,573  6/1976  Stauffer .................................... 195/2

Primary Examiner—Alvin Tanenholtz
Attorney, Agent, or Firm—Cushman, Darby & Cushman

[57] ABSTRACT

A method for optical resolution of DL-lysine alkyl ester or acid-addition salts thereof by contacting an aqueous solution of the ester or salts thereof with a non-specific protease obtained by culturing bacteria belonging to the genus Streptomyces, e.g. *St. griseus*, at weakly acidic pH and a temperature not exceeding 60° C until 60 – 90% by weight of L-lysine ester or acid-addition salts thereof takes part in a reaction, and recovering L-lysine or acid-addition salts thereof thus produced by a conventional manner. The protease may be immobilized on an insoluble carrier in advance.

20 Claims, No Drawings

METHOD FOR OPTICAL RESOLUTION OF DL-LYSINE COMPOUNDS

This invention relates to a method for producing L-lysine or an acid-addition salt thereof by optical resolution of a DL-lysine alkyl ester or an acid-addition salt thereof, through enzymatic asymmetric hydrolysis.

An amino acid synthetically produced is, in general, in the racemic form. Optical resolution of this racemic form, therefore, poses a serious problem.

So far as optically active L-lysines are concerned, there have been known the following methods: (1) a method in which a salt is formed from DL-lysine and other optically active acid and L-lysine is selectively crystallized from the resultant salt, (2) a method in which an optically active compound is immobilized on an insoluble carrier, thereby L-isomer is chromatographically separated from D-isomer by making effective use of the difference of affinity between the two isomers, (3) a method in which DL-lysine is converted into an N-acyl compound and subsequently the N-acyl compound is resolved with an aminoacylase into L-lysine and N-acyl-D-lysine and (4) a method in which DL-lysine is converted into an alkyl ester or an acid-addition salt thereof and said ester or salt is enzymatically, asymmetrically hydrolyzed with an esterase for thereby resolving the ester or salt into L-lysine and D-lysine alkyl ester. There have also been made various efforts in order to render these methods economically feasible. The methods of (1) and (2) are economically problematic because it is difficult to obtain products which are satisfactory in terms of both yield and optical purity. The method of (3) is fairly effective in the production of many amino acids. In the case of lysine, however, the enzyme does not function effectively unless the amino group at the ε position of this particular amino acid is protected with a considerably bulky substituent such as benzoyl group, for example. With respect to the method of (4), resolution of DL-lysine by use of an immobilized trypsin has been specifically proposed, for example (Japanese Laid-Open Patent Publication No. 13390/1974). Indeed trypsin possesses specificity and high activity toward basic amino acids. Trypsin purified by crystallization is very expensive, and an attempt at obtaining a large amount of the purified trypsin entails unusual difficulty. Moreover, the enzyme is so unstable that it is readily inactivated, for example, by mere agitation given thereto in water to facilitate its solution in water. Even in the neighborhood of its optimum pH value, the enzyme is fairly rapidly inactivated. Thus, it cannot justly be said that this enzyme is suitable for use on a commercial scale. Furthermore, although the resolution by use of esterases including trypsin has superiority in a reaction velosity when it is carried out in the range of the optimum pH, the difficulty is encountered that a D-form amino acid ester is hydrolysed non-enzymatically, making it difficult to obtain the L-amino acid with high optical purity. Since enzymes having the esterase activity generally show their optimum pH values at the level of 7 or higher, and the enzymatic reactions proceed in a slightly alkaline pH range, there is frequently accompanied by a non-enzymatic hydrolysis of the esters. Consequently, the enzymatic reactions have to be carried out in a slightly acidic pH range where the enzymes have low activities.

The present inventors have found that a nonspecific protease produced by bacteria of the genus *Streptomyces* exhibits a powerful esterase activity to a lysine alkyl ester having an unacylated nitrogen at the α position and is effective for the purpose of said resolution. Heretofore, proteases were said to have no specificity on optical isomerism with respect to amino acid esters of the class having no acylated nitrogen atom in the amino group. Besides, more often than not, proteases of microorganic origin exhibit less rigid specificity on substrate than similar enzymes of animal origin. For these reasons, examples of optical resolution by use of proteases of microorganic origin are not very numerous. However, non-specific proteases produced by bacteria of the genus *Streptomyces* are found to exhibit a very high activity to the L-form lysine ester as compared to the activity to the D-form isomer. Furthermore, the present enzymatic reaction proceeds very efficiently in a slightly acidic pH range and substantially no non-enzymatic spontaneous hydrolysis proceeds. In the hydrolysis of lysine alkyl ester with the non-specific protease produced by bacteria of the genus *Streptomyces*, the optimum pH value falls in the range of around 5.7.

According to the present invention, a method of producing L-lysine or acid-addition salts thereof from DL-lysine alkyl ester or acid-addition salts thereof through enzymatic optical resolution, which comprises contacting an aqueous solution of the DL-lysine alkyl ester or acid-addition salts thereof with a non-specific protease having ability to resolve the DL-lysine alkyl ester or acid-addition salts thereof produced by culturing a microorganism of *Streptomyces sp.*, under a weakly acidic condition at a temperature lower than 60° C, and recovering L-lysine or acid-addition salts thereof thus produced.

The substrate, DL-lysine alkyl ester or acidaddition salts thereof, is prepared by any known method. For example, from DL-lysine and an alcohol, the ester can be synthesized. A synthesis may also be started with cyclohexanone to obtain the ester as the precursor not through the DL-lysine itself. The number of carbon atoms in the alkyl moiety of the lysine ester is desired to be in the range of from 1 to 6. Preferable alkyl moieties are methyl, ethyl, n-propyl, isopropyl, n-butyl, secondary butyl and tertiary butyl groups. Methyl and ethyl are most preferable. As the number of carbon atoms increases, the ester and the acid-addition salt thereof become sparingly soluble in water and the velocity of the hydrolysis to be effected on said ester and said salt with the enzyme is lowered.

As the reaction medium, it is advantageous to use water since lysine alkyl esters or acid-addition salts thereof are readily soluble therein. Non-aqueous solvents such as alcohols which are miscible with water may be allowed to coexist with water, on condition that their presence does not notably obstruct the enzymatic activity. Generally, a neutral salt or salts having buffer action are allowed to coexist in the reaction medium for the purpose of permitting required adjustment of the pH value of the reaction system. The concentration of the substrate in the aqueous solution is not particularly critical. An increase of the substrate concentration very close to the solubility of the substrate does not prove desirable for the enzymatic activity, although it serves the purpose of facilitating the recovery of the reaction product. It is, therefore, necessary that a suitable substrate concentration should be determined by taking these factors into consideration. Desirably the concentration may be selected from the range of from 100 mg/ml to 500 mg/ml.

The amount of the non-specific protease to be used is variable with the degree of purification and the activity involved, but this enzyme need not be used in a large amount. The amount is sufficient in the order of 0.3 to 3%, particularly 0.1 to 1.5%, by weight based on the amount of the substrate. The non-specific protease may be used in the immobilized form on an insoluble carrier. The weight of the non-specific protease relative to that of the produced amino acid is much smaller than the weight which is in conformity with the proportion mentioned above, because the enzyme can be used repeatedly.

Any of the bacteria of genus *Streptomyces* that produce non-specific proteases can be effectively used insofar as it is able to produce an enzymatic component which exhibits activity to the lysine alkyl ester. Particularly, *Streptomyces griseus, Streptomyces fradiae, Streptomyces erythreus, Streptomyces rimosus* and *Streptomyces flavovirens* are advantageously used since they produce highly active lysine alkyl ester hydrolases.

With regard to the immobilization of the nonspecific protease, there can be applied any of the methods heretofore known as available for the purpose. The requirement to be met at all is that the non-specific protease immobilized to the insoluble carrier should retain an activity relative to the asymmetric hydrolysis of the DL-lysine alkyl ester or acid-addition salt thereof. Owing to the immobilization of the enzyme, the enzyme which has heretofore been used in a homogeneous reaction system in a solution and, as a natural consequence, discarded at the end of each batchwise use can be used repeatedly or continuously. Thus, the immobilization of the enzyme brings about outstanding economic advantages such as economization of the amount of enzyme consumed, reduction in the amount of secondarily produced waste and simplification of the process involved in the purification of the product.

As the prior techniques for the immobilization of enzymes, there can be cited (as described by O. R. Zaborsky in the Immobilized Enzymes, C. R. C. Press, 1973) (1) ionic or physical adsorption method, (2) covalent attachment method, (3) entrapment method and (4) crosslinking method. The ionic or physical adsorption method is convenient for commercial applications because it is simple. This method, however, entails a possibility that the enzyme will be liberated from the carrier when the ion strength and the concentrations of substrate and product in the reaction solution are high. In this respect, the immobilization by the covalent attachment method of (2) rarely experiences such liberation of the enzyme once the enzyme is immobilized, although the preparation of immobilized enzyme itself is rather complicated. It may be safely said that this method proves advantageous where both substrates and the products or one of those are ionic substances. Therefore, this method can be used for the resolution of lysine compounds effectively. Concerning the methods of classes (3) and (4), the former method is problematic in respect of its capacity for preservation of activity because the enzyme involved happens to be a protease and the latter method does not provide any notably good results as compared to the covalent attachment method. All considered, among all the methods of the four classes (1) through (4), the method which makes use of the covalent attachment proves to be most desirable for the reaction system to be involved.

For the purpose of the immobilization, the nonspecific protease can be used in its purified form as well as in its crude form. Further, the enzyme component which exhibits an activity to the lysine alkyl ester can be used in its isolated form or in the mixture form wherein said enzyme component coexists with other protease components. The reaction can be carried out batchwisely, in which case, upon termination of the hydrolysis, the immobilized enzyme is separated from the reaction solution by filtration or centrifugation so as to be used again in the subsequent batch of operation. Alternatively, the hydrolysis can be continuously carried out by having the immobilized enzyme packed in a column in advance and allowing the substrate in the form of a solution to be passed continuously through the column either in the downward direction from the upper end of the column or in the reverse direction. In the batchwise reaction, the pH adjustment of the reaction solution is easily obtained. In the continuous reaction in a column, the reaction can be easily continued.

In the method of the present invention, a reaction temperature of not higher than 60° C will suffice. If the reaction is carried out at a high temperature, the enzyme tends to undergo inactivation, although the reaction velocity is increased. In addition, the reaction entails an undesirable phenomenon of non-enzymatic hydrolysis. Thus, the temperature which proves to be advantageous from the practical point of view must be determined by taking into consideration the wisdom of balancing all of these factors. The reaction temperature is particularly advantageous in the range of from 20° C to 45° C and, in this temperature range, the immobilized non-specific protease enjoys high stability.

The present process is effected under weakly acidic conditions, because optimum pH for the non-specific protease is about 5.7.

The reaction velocity of the hydrolysis of the lysine alkyl ester by use of the non-specific protease goes down in proportion as the duration of the reaction increases. The reaction velocity is extremely lowered after about 80% of the L-form isomer has undergone the hydrolysis. It is, therefore, both advantageous and desirable from the economic point of view to terminate the reaction of the L-form isomer after it has proceeded to a range of from 60 to 90% instead of leaving the reaction to proceed to 100%.

No matter whether the enzyme is used in the form of a solution or in an immobilized form, the acquisition of L-lysine or an acid-addition product thereof from the hydrolyzate containing D-lysine alkyl ester or an acidaddition salt thereof and unaltered L-lysine alkyl ester or an acid-addition salt thereof can be accomplished by using any of various methods known to the art. For example, it is effected by a procedure comprising the steps of adding to the reaction solution an alcohol of a volume about 10 to 20 times as large, concentrating the alcoholic solution to cause precipitation of the acid-addition product of L-lysine and separating the precipitate by filtration. Alternatively, the reaction solution is first concentrated, then an alcohol or acetone is added in order to precipitate the acid-addition product of L-lysine which is separated by filtration. Unaltered lysine alkyl ester can be recovered by extracting it with some organic solvent for the ester such as, for example, ethyl acetate or by dissolving it in an alcohol, then adding ether or toluene for thereby causing precipitation and separating the precipitate by filtration. The acid-addition salt of lysine alkyl ester obtained as described above may be racemized, as occasion demands, and put to re-use.

The present invention will be described in further detail with reference to examples.

EXAMPLE 1

In 20 ml of 0.004M monopotassium phosphate solution, 3.0 g of DL-lysine methyl ester dihydrochloride was dissolved. The resultant solution was adjusted to pH 6.0 addition of 1N sodium hydroxide solution. To the solution, 1 ml of an enzyme solution containing 36 mg of Pronase (non-specific protease) obtained from *Streptomyces griseus* was added to start an emzymic reaction. The hydrolysis was allowed to proceed at 30° C, with the pH value of the reaction solution kept at 6.0 by addition of a 1N sodium hydroxide solution. After lapse of a period of 25 minutes which a calculation performed on the basis of the amount of sodium hydroxide added to the reaction system showed as necessary for the reaction to proceed to the extent of consuming about 39% of the DL-lysine methyl ester, the reaction was stopped by adding methanol twice as much of the reaction solution to the reaction system. The solvent was expelled through evaporation from the reaction solution by heating the solution at temperatures not exceeding 50° C, and the residue obtained from the evaporation was dissolved in a small amount of methanol to permit separation of insolubles by filtration. The insolubles were dissolved in water, and an amount of trichloroacetic acid corresponding to 5% by weight was added thereto. Subsequently, the insoluble enzyme was removed by centrifugal separation. Further, the aqueous solution was evaporated to a final volume of about 1 ml. The evaporation residue was mixed with about 15 ml of methanol. The precipitate consequently formed in the mixture was filtered off, washed and dried to afford 1.20 g of purified crystals of L-lysine dihydrochloride. This product was found to have specific optical rotation, $[\alpha]_{546}^{20°\,C}$, of +20.0 (C = 2, 6N-HCl), as compared with the standard pure L-form substance which has specific optical rotation, $[\alpha]_{546}^{20°\,C}$, of +20.4 (C = 2, 6N-HCl). This means that the selectivity for the purified L-lysine was 99%. In the meantime, the ester which had as its main component, the D-lysine methyl ester dihydrochloride in the initial filtrate was withdrawn by adding ether to the filtrate for thereby causing precipitation of said dihydrochloride and crystallizing out the precipitate. Specific optical rotation, $[\alpha]_{546}^{20°\,C}$, of the crystals was found to be −12.4 (C = 2, 6N-HCl).

EXAMPLE 2

In place of the enzyme used in Example 1, there was used 40 mg of a non-specific protease which was obtained as described below. By an ordinary method, *Streptomyces fradiae* was cultured in a Basal medium for three days. The culture broth was filtered, salted out with ammonium sulfate (60% saturated solution), precipitated in acetone, then refined by a chromatographic treatment using DEAE-cellulose in accordance with the procedure reported in Biochim. Biophs. Acta, 139, 382 (1967) with necessary modifications and thereafter lyophilized. The reaction was carried out under the same conditions as those of Example 1. The reaction was stopped after 78% of the L-form had been used up in the reaction. The reaction solution was treated by the procedure of Example 1 to afford 1.04 g of purified L-lysine dihydrochloride. This was shown to have specific optical rotation, $[\alpha]_{546}^{20°\,C}$, of +19.8 (C = 2, 6N-HCl), indicating that the selectivity was 98.5%.

EXAMPLE 3

In 40 ml of water, 1 g of Sephalose 4B (Farmacia) was immersed in conjunction with 1 g of cyanogen bromide at pH 11 and 15° C for 15 minutes to have Sephalose 4B activated. Then, the mixture was held in contact with the enzyme Pronase at pH 7.4 at room temperature for two hours, to afford an immobilized enzyme containing 23 mg of the enzyme. The activity of this immobilized enzyme to DL-lysine methyl ester dihydrochloride at 40° C was 2.5 μ.moles/mg.min, which corresponds to 40% of that of the enzyme in the form of a solution. This immobilized enzyme was packed in a jacketed column. With the column maintained at 30° C, a 10% solution of DL-lysine methyl ester dihydrochloride in a phosphate buffer sulution at pH 6.85 was fed upflow from through the lowest portion of the column at space velocity of 8.6 hr$^{-1}$. By the quantitative analysis of the effluent from the column head for its ester content by the hydroxamic acid process, the conversion relative to the DL-form was found to be 40.5% (81% relative to the L-form). The effluent was mixed with a volume of alcohol several times as large to cause precipitation of salts which were removed by filtration. The filtrate was concentrated and was again mixed with a volume of alcohol about 15 times as large to produce a precipitate (I). Specific optical rotation, $[\alpha]_{546}^{20°\,C}$, of the precipitate was found to be +15.6 (C = 2, 6N-HCl). This precipitate (I) was purified by recrystallization from water-alcohol to produce crystals (II) having specific optical rotation, $[\alpha]_{546}^{20°\,C}$, of +19.7. When the filtrate remaining after the separation of the precipitate (I) was evaporated to expel methanol therefrom, the residue was found to have specific optical rotation, $[\alpha]_{546}^{20°\,C}$, of −6.7.

EXAMPLE 4

In methanol, 2 g of a macroporous weakly acidic cation-exchange resin of acrylic acid-divinylbenzene copolymer (having an exchange group of —COOH and a particle size of 24 mesh) was esterified with thionyl chloride by an ordinary method and thereafter converted into hydrazide with hydrazine hydrate. In 1N hydrochloric acid, this resin was allowed to react with 2.1 g of sodium nitrite at 2° C for 1 hour to produce an azide. In an aqueous solution of the enzyme (containing 155 mg of the enzyme) prepared in advance from *Streptomyces fradiae*, the azidized resin was placed and agitated at pH 7.5 and 4° C for 4 hours to have the enzyme immobilized on the resin. The immobilized enzyme on the resin was washed with a 0.2M buffer solution and a 5M NaCl solution to find an amount of enzyme immobilized to be 47 mg per g of the carrier. A test for dependency of the enzyme activity upon pH revealed that the optimum pH value had shifted to a range of 6.5 to 6.7. In 20 ml of a 0.1M potassium chloride solution, 4.12 g of DL-lysine ethyl ester dihydrochloride was dissolved. The aforementioned immobilized enzyme was added to the solution and the mixture was agitated to 35° C with the pH value thereof kept at 6.6 by addition of a 1N NaOH solution. After 40 minutes of the agitation, the immobilized enzyme was separated by filtration and the remaining solution was concentrated by evaporation to about 5 ml. To the concentrate was added 95 ml of ethanol. The precipitate which occurred consequently therein was separated by filtration, washed and dried to afford 1.67 g of L-lysine dihydrochloride, which was found to have specific optical rotation, $[\alpha]_{546}^{20°\,C}$, of +19.1 (C = 2, 6N-HCl). The 95% ethanol solution of the filtrate was evaporated and the residue (slightly hygroscopic) was found by a test to have specific optical rotation, $[\alpha]_{546}^{20° C}$, of −4.5 (C = 2, 6N-HCl).

EXAMPLE 5

In 1N NaOH, 2 g of Sephadex G-25 (dextranepichlorohydrin copolymer made by Pharmacia Co.) was immersed. Then the copolymer was separated by filtration. It was allowed to react with cyanuric chloride for 15 seconds in dioxane. The reaction mixture was washed with cold acetone and ice water and then 200 mg of the enzyme Pronase E was dissolved therein. In a borate buffer solution, the s-triazine derivative of Sephadex G-25 obtained as described above was immersed and gently agitated for 5 hours at pH 8.0 and 4° C to have the enzyme Pronase immobilized. The amount of the enzyme immobilized was 67 mg per g of carrier and the specific activity of the immobilized enzyme at 40° C and pH 6.0 was found to be 2.53 μ.moles/mg.min. The optimum pH of this immobilized enzyme on DL-lysine methyl ester dihydrochloride as the substrate was found to be around 6.1. The immobilized enzyme was packed in a jacketed column. With the column temperature kept at 40° C, 50 ml of a DL-lysine methyl ester dihydrochloride solution having a concentration of 10% and kept at pH 6.8 was fed downflow from the column head at space velocity of 13 hr$^{-1}$. pH of the effluent was lowered to 5.75 as the reaction proceeded. When the effluent from the column was tested for conversion by the ninhydrin process under conditions selected so as to permit coloration with amino acids and no coloration with amino acid esters, it was revealed that 40% of the DL-form had undergone the reaction. The effluent was mixed with a volume of methanol about four times as large, and the salt consequently precipitated therein was removed. Thereafter, the mixture was concentrated to about 20 ml by evaporation of the solvent. To the concentrate was added about 100 ml of acetone to produce 2.02 g of L-lysine dihydrochloride in the form of precipitate. This salt was found to have specific optical rotation, $[\alpha]_{546}^{20° C}$, of +15.8 (C = 2, 6N-HCl). When it was recrystallized from watermethanol, the purified product showed a specific optical rotation of +19.2. This operation of the resolution by use of the column described above was performed a total of ten cycles over a period of 15 days with the same space velocity. During the period, the specific optical rotation of the precipitate remained unchanged, although the conversion tested by the ninhydrin process fell to eventually 30% of the DL-form.

EXAMPLES 6 – 10

The enzyme was immobilized by various methods, and with the resultant immobilized enzymes, DL-lysine methyl ester dihydrochloride was resolved. The results are tabulated herein below. The conditions for immobilization, the determination of amounts of bound enzymes and the method for precipitating L-lysine dihydrochloride and recrystallizing the precipitate were the same as those described in Examples 1 – 5.

| Example No. | Carrier | Method of binding | Amount of immobilized enzyme (mg of enzyme/g of carrier) | Method of reaction | Reaction temperature (° C) | Reaction time (min.) |
|---|---|---|---|---|---|---|
| 6 | Duorite A-4 | Azide process | 55 | Batch | 30 | 35 |
| 7 | Sephalose 4B | Cyanogen bromide process | 40 | Column | 40 | — |
| 8 | Duorite A-6 | S-triazine process | 87 | Batch | 30 | 25 |
| 9 | Duorite A-7 | S-triazine process | 83 | Column | 40 | — |
| 10 | Duorite S-37 | S-triazine process | 223 | Batch | 40 | 30 |

| Space velocity (1/hr) | Amount of substrate solution (ml) | Concentration of ester (%) | Specific optical rotation $[\alpha]_{546}^{20° C}$, of first precipitate (C = 2, 6N-HCl) | Specific optical rotation $[\alpha]_{546}^{20° C}$, of residue from evaporation of filtrate (C = 2, 6N-HCl) | Specific optical rotation $[\alpha]_{546}^{20° C}$, of recrystallized precipitate (C = 2, 6N-HCl) |
|---|---|---|---|---|---|
| — | 40 | 10 | +18.7 | −8.7 | — |
| 9.0 | 50 | 10 | +15.2 | −5.7 | +18.8 |
| — | 50 | 10 | +18.1 | −9.5 | +19.9 |
| 12.5 | 50 | 20 | +13.8 | −4.6 | +18.3 |
| — | 50 | 20 | +17.2 | −9.1 | +20.0 |

What is claimed is:

1. A method for producing L-lysine or acidaddition salts thereof from DL-lysine alkyl ester or acid-addition salts thereof, which comprises contacting under a weakly acidic condition an aqueous solution of the DL-lysine alkyl ester or acid-addition salts thereof with a non-specific protease having ability to resolve the DL-lysine alkyl ester or acid-addition salts thereof and being produced by bacteria belonging to the genus Streptomyces and recovering L-lysine or acid-addition salts thereof thus produced.

2. A method according to claim 1 wherein bacteria belonging to the genus Streptomyces is *St. griseus, St. fradiae, St. erythreus, St. rimosus* or *St. flavovirens.*

3. A method according to claim 1 wherein the contacting is terminated before all of L-lysine alkyl ester or acid-addition salts thereof is consumed.

4. A method according to claim 3 wherein the contacting is terminated when 60 – 90% of L-lysine alkyl ester or acid-addition salts thereof is consumed.

5. A method according to claim 1 wherein pH at the time of contacting is about 5.7.

6. A method according to claim 1 wherein the alkyl has 1 to 6 carbon atoms.

7. A method according to claim 6 wherein the alkyl has 1 to 4 carbon atoms.

8. A method according to claim 7, wherein the alkyl has 1 to 2 carbon atoms.

9. A method according to claim 1 wherein the concentration of the DL-lysine alkyl salt or acid-addition salts thereof in an aqueous solution is from 100 mg/ml to 500 mg/ml.

10. A method according to claim 1 wherein a neutral salt or salts having buffer action is allowed to be present in the aqueous solution, in order to control pH of the reaction.

11. A method according to claim 1 wherein the contacting is carried out at a temperature lower than 60° C.

12. A method according to claim 11 wherein the temperature is 20° to 45° C.

13. A method according to claim 1 wherein the aqueous solution contains non-aqueous, water-miscible solvents.

14. A method according to claim 1 wherein the protease is immobilized on a solid carrier.

15. A method according to claim 14 wherein the protease is immobilized on a solid carrier by covalent attachment method.

16. A method according to claim 14 wherein the contacting is carried out batchwisely.

17. A method according to claim 16 wherein the contacting is effected under pH of 5.0 to 7.0.

18. A method according to claim 14 wherein the contacting is effected in a continuous manner using a column or columns.

19. A method according to claim 18 wherein a solution of a substrate to be fed to the column has pH 5.0 to 7.0.

20. A method according to claim 19 wherein salts having buffer action are allowed to coexist in the substrate solution.

* * * * *